United States Patent
Marshall, III et al.

(10) Patent No.: US 6,458,112 B1
(45) Date of Patent: Oct. 1, 2002

(54) COMPOUND SANITARY NAPKIN HAVING FLAPS AND ZONE OF EXTENSIBILITY

(75) Inventors: Robert E Lee Marshall, III, Ashiya; Jin-Young Song, Higashinada-Ku Kobe; Nami Terada, Kobe, all of (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/555,587

(22) PCT Filed: Dec. 5, 1997

(86) PCT No.: PCT/US97/22287

§ 371 (c)(1),
(2), (4) Date: Jun. 1, 2000

(87) PCT Pub. No.: WO99/29274

PCT Pub. Date: Jun. 17, 1999

(51) Int. Cl.⁷ ............................................. A61F 13/15
(52) U.S. Cl. .................................... 604/385.1; 604/386
(58) Field of Search ........................... 604/385.1, 386, 604/387

(56) References Cited

U.S. PATENT DOCUMENTS

| | | | |
|---|---|---|---|
| 2,331,355 A | | 10/1943 | Strongson |
| 4,425,130 A | | 1/1984 | DesMarais |
| 5,344,416 A | * | 9/1994 | Niihara et al. ......... 604/385.04 |
| 6,280,428 B1 | * | 8/2001 | Lash et al. ............. 604/385.03 |
| 6,328,722 B1 | * | 12/2001 | Lavash et al. ......... 604/385.04 |

FOREIGN PATENT DOCUMENTS

| | | |
|---|---|---|
| EP | 0 511 905 A1 | 11/1992 |
| EP | 0 965 542 A1 | 2/1996 |
| EP | 0 768 072 A1 | 4/1997 |
| WO | WO 93/06805 A1 | 4/1993 |
| WO | WO 93/06805 | 4/1993 |
| WO | WO 94/02096 | 2/1994 |
| WO | WO 95/08311 A1 | 3/1995 |
| WO | WO 95/20932 A1 | 8/1995 |
| WO | WO 95/28137 | 10/1995 |
| WO | WO 95/28137 A2 | 10/1995 |
| WO | WO 96/03948 A1 | 2/1996 |
| WO | WO 96/25903 | 8/1996 |
| WO | WO 97/14390 A1 | 4/1997 |

\* cited by examiner

Primary Examiner—Andy Falik

(57) ABSTRACT

The present invention relates to a compound sanitary napkin (20) comprising a primary absorbent member (30), a base member (50), flaps (33) and at least one zone of extensibility (66). The compound sanitary napkin (20) has a longitudinal center line along a longitudinal direction and a transverse center line along a transverse direction. The primary absorbent member (30) has a longitudinal length (PL), a transverse width (PW), a thickness (PT), a pair of longitudinal sides (24) and a pair of transverse ends (25), and comprises a primary absorbent element (30) and a fluid pervious cover (32) superimposed on the primary absorbent element (30). The base member (50) has a longitudinal length, a transverse width, a thickness, a pair of longitudinal sides (21) and a pair of transverse ends, and comprises a fluid pervious body-facing sheet (52) and a fluid impervious garment-facing sheet (54) joined to the fluid pervious body-facing sheet (52), the primary absorbent member (30) is joined to the base member (50) at least at a part of the longitudinal direction of the primary absorbent member (30). Flaps (33) extend laterally outwardly from the longitudinal sides of the base member (50). Each of the flaps (33) has a proximal edge (40) joined with the longitudinal sides (21) of the base member (50), a distal edge (41) spaced laterally outwardly from the proximal edge (40). The flaps (33) cover a portion of the leg openings of the wearer's undergarment. At least one zone of extensibility (66) comprises at least a portion of the flaps (33), wherein at least a portion of the zone of extensibility (66) is spaced longitudinally away from the flap transverse centerline. The entire length of the proximal edge of the flaps (33) is not less than 20% of the length of the primary absorbent member (30). At least the zone of extensibility (66) is extensible to be capable of a stress given to the flap (33) when the compound sanitary napkin (20) is worn so that the flaps (33) are relatively free from shifting when at least a portion of the primary absorbent member (30) shifts away from the flap (33).

9 Claims, 8 Drawing Sheets

COMPOUND SANITARY NAPKIN HAVING FLAPS AND ZONE OF EXTENSIBILITY

FIELD OF THE INVENTION

The present invention relates to a body fitting compound sanitary napkin having flaps and zones of extensibility. More particularly, the invention relates to a compound sanitary napkin comprising a primary absorbent member, a base member having flaps and zones of extensibility.

BACKGROUND

In their simplest form, disposable sanitary napkins comprise an absorbent element (sometimes referred to as an absorbent core) interposed between a fluid pervious body-facing sheet (sometimes referred to as a topsheet) and a fluid impervious garment-facing sheet (sometimes referred to as a backsheet). The absorbent element is, of course, intended to receive and contain menses and other vaginal discharges. The body-facing sheet is intended to provide more or less comfortable and dry-feeling contact with body surfaces while allowing free passage of fluids therethrough into the absorbent element. The garment-facing sheet is intended to prevent menses or other vaginal discharges which are expelled or which escape from the absorbent element from soiling the wearer's undergarments. In addition to the three functional elements mentioned above, disposable sanitary napkins are generally provided with means for supporting the device adjacent the wearer's crotch area, even as the wearer moves, where it can most effectively perform its intended function. Typically, sanitary napkins are provided with an adhesive attachment means for securing the device to the inner crotch area of the wearer's undergarments.

While previously known sanitary napkins do perform their intended function, each conventional design suffers from certain deficiencies in one or more of absorbency of body fluids, protection of the wearer's undergarments from soiling, and/or physical comfort to the wearer.

With respect to disposable sanitary napkins, at least two general classes presently exist. One such class is identified as being intended for the absorption of medium to high menstrual flows. These sanitary napkins offer a relatively high absorptive capacity. Absorptive capacity is commonly achieved by providing the sanitary napkin with a relatively thick and bulky absorbent member. While having a relatively high absorptive capacity, the bulkiness of the absorbent member may cause a certain degree of wearing discomfort. A second class of sanitary napkins are intended for light or low menstrual flows and are commonly referred to as pantiliners or pantishields. Sanitary napkins of this class, as a group, are thinner, somewhat more flexible and generally more comfortable than those of the first class. However, sanitary napkins of the second class typically lack the absorptive capacity of sanitary napkins of the first class.

One attempt to provide the benefits of the previously described two classes of sanitary napkins into a single compound sanitary napkin is disclosed in commonly assigned U.S. Pat. No. 4,425,130 issued to DesMarais on Jan. 10, 1984. The compound sanitary napkin of DesMarais comprises a primary menstrual pad and a panty protector joined to one another.

On the other hand, sanitary napkins having flaps are widely known. Such flaps are folded to secure the outside of the wearer's undergarment. The flaps serve prevention of soiling the edges of the undergarment. Therefore, the longer the flaps, the less soiling the undergarment is expected. However, as the flaps becomes longer, it becomes difficult for the flaps to be folded along the edges of the undergarment.

While prior art sanitary napkins have addressed some of the problems of achieving a compound sanitary napkin, they have not addressed the problems to the extent of or in the manner of the present invention. Therefore, a primary objective of the present invention is to provide a compound sanitary napkin having flaps and zone of extensibility.

SUMMARY

The present invention relates to a compound sanitary napkin comprising a primary absorbent member, a base member, flaps and at least one zone of extensibility. The compound sanitary napkin has a longitudinal center line along a longitudinal direction and a transverse center line along a transverse direction. The primary absorbent member has a longitudinal length, a transverse width, a thickness, a pair of longitudinal sides and a pair of transverse ends, and comprises a primary absorbent element and a fluid pervious cover superimposed on the primary absorbent element. The base member has a longitudinal length, a transverse width, a thickness, a pair of longitudinal sides and a pair of transverse ends, and comprises a fluid pervious body-facing sheet and a fluid impervious garment-facing sheet joined to the fluid pervious body-facing sheet. The primary absorbent member is joined to the base member at least at a part of the longitudinal direction of the primary absorbent member. Flaps extends laterally outwardly from the longitudinal sides of the base member. Each of the flaps has a proximal edge joined with the longitudinal sides of the base member, a distal edge spaced laterally outwardly from the proximal edge. The flaps cover a portion of the leg openings of the wearer's undergarment. At least one zone of extensibility comprises at least a portion of the flaps, wherein at least a portion of the zone of extensibility is spaced longitudinally away from the flap transverse centerline. The entire length of the proximal edge of the flaps is not less than 20% of the length of the primary absorbent member. At least the zone of extensibility is extensible to be capable of a stress given to the flap when the compound sanitary napkin is worn so that the flaps are relatively free from shifting when at least a portion of the primary absorbent member shifts away from the flap.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

This invention relates to a body fitting compound sanitary napkin which exhibits absorbency for bodily fluids, the protection of the wearer's undergarments from soiling, and physical comfort to the wearer. More particularly, the present invention relates to a body fitting compound sanitary napkin comprising a primary absorbent member, a base member, flaps, and zones of extensibility. The term "sanitary napkin", as used herein, refers to an article which is worn by females adjacent to the pudendal region and which is intended to absorb and contain the various exudates which are discharged from the body (e.g., blood, menses, and urine) and which is intended to be discarded after a single use (i.e., it is not intended to be laundered or otherwise restored or reused). The term "compound sanitary napkin", as used herein, refers to a sanitary napkin comprised of separate constituents joined to one another to form a unitary structure. Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
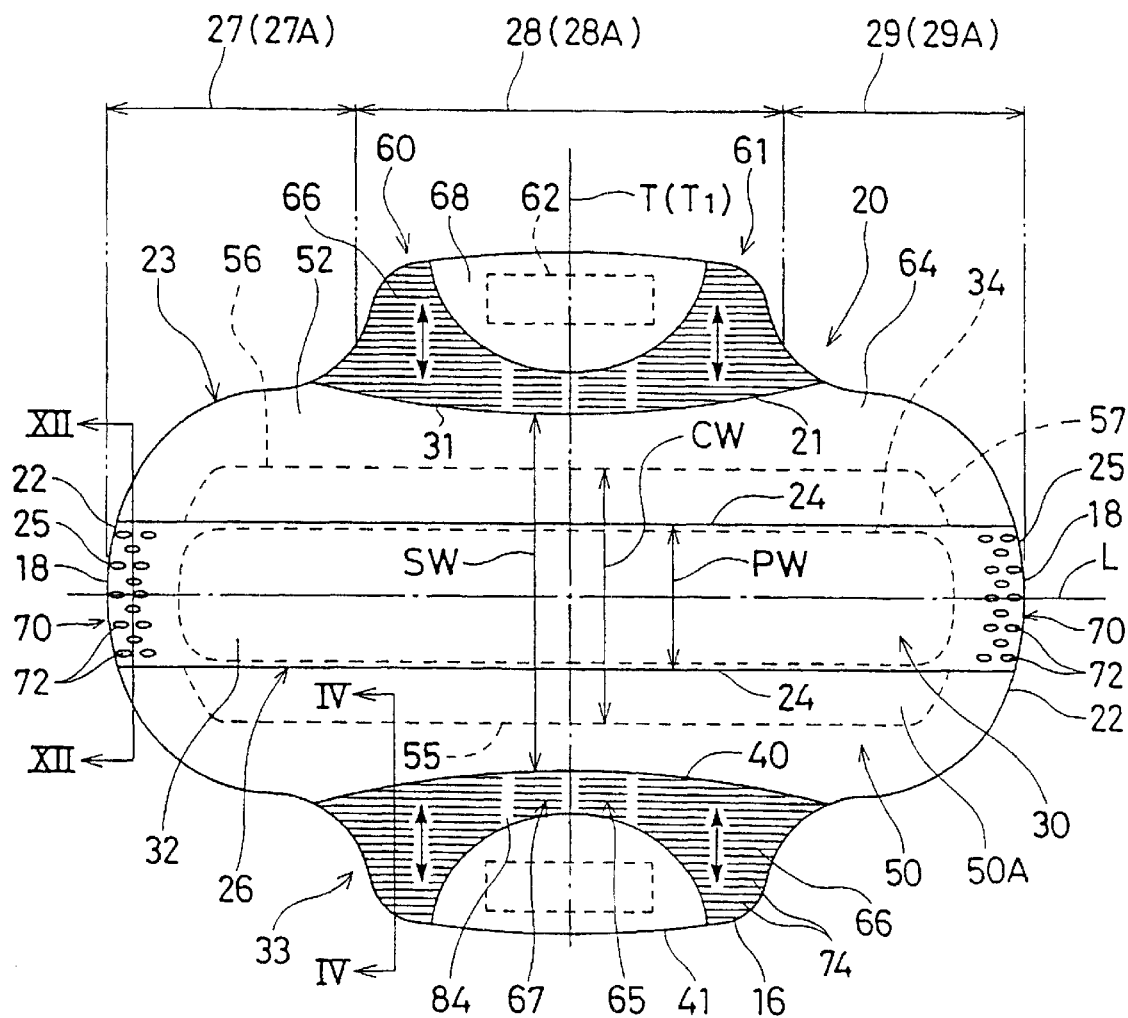
FIG. 1 is a top plan view of one embodiment of the compound sanitary napkin of the present invention.
Figure 2:
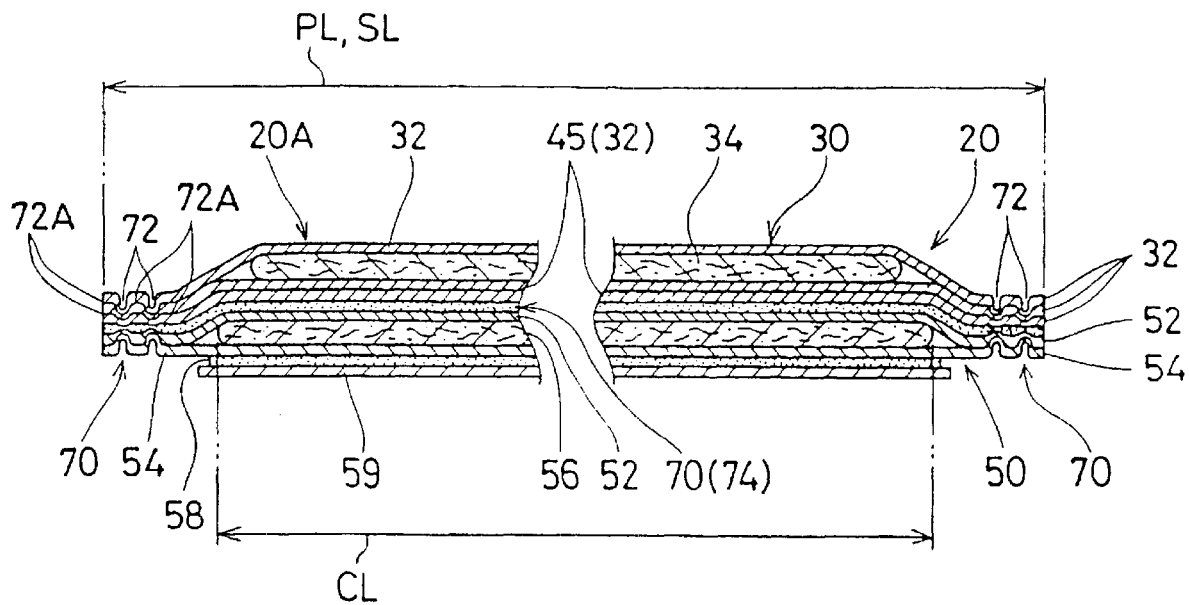
FIG. 2 is a cross-sectional view taken along the longitudinal centerline L of the compound sanitary napkin shown in FIG. 1.
Figure 3:
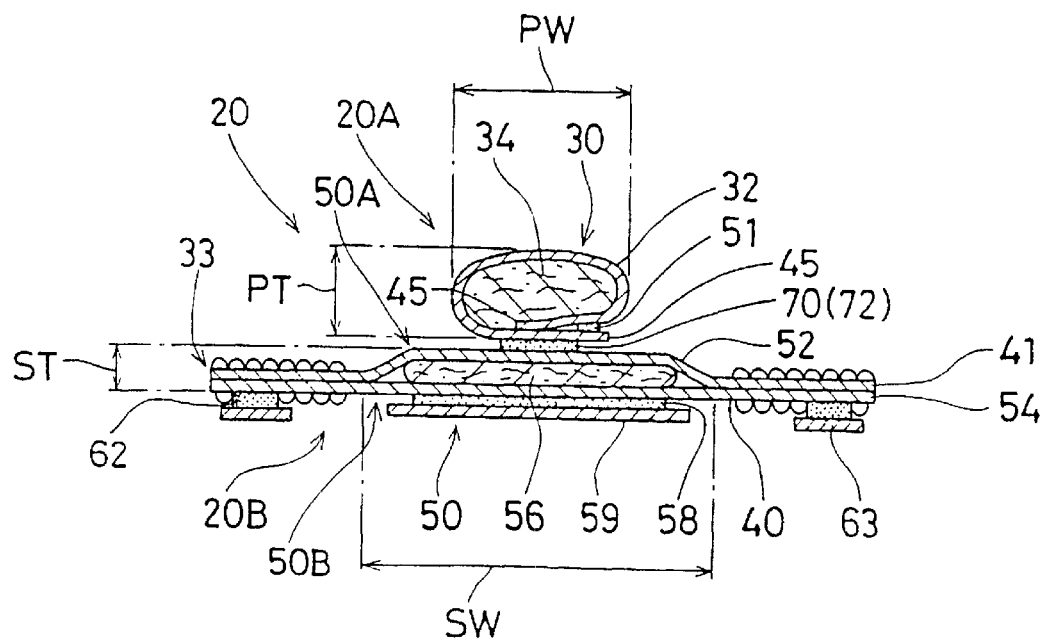
FIG. 3 is a cross-sectional view taken along the transverse centerline T of the compound sanitary napkin shown in FIG. 1.
Figure 4:
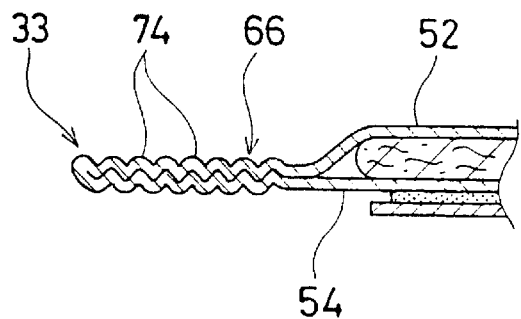
FIG. 4 is a cross-sectional view taken along line IV—IV shown in FIG. 1.

A preferred embodiment of a compound sanitary napkin is described. Referring now to FIGS. 1–3, there is shown one preferred embodiment of a compound sanitary napkin 20. The compound sanitary napkin 20 has two surfaces, a body contacting or facing surface 20A, and a garment contacting or facing surface 20B. In a preferred embodiment shown in FIG. 1, the compound sanitary napkin 20 has a first end region 27, a central region 28, a second end region 29, longitudinal sides 16 and transverse ends 18. The compound sanitary napkin 20 has two centerlines, a longitudinal centerline L and a transverse centerline T. The term "longitudinal", as used herein, refers to a line, axis or direction in the plane of the compound sanitary napkin that is generally aligned with (e.g., approximately parallel to) a vertical plane which bisects a standing wearer into left and right body halves when the compound sanitary napkin is worn. The terms "transverse" or "lateral", as used herein, are interchangeable, and refer, to a line, axis, or direction which lies within the plane of the compound sanitary napkin that is generally perpendicular to the longitudinal direction.

As can be seen in FIGS. 1–3, the compound sanitary napkin 20 comprises a primary absorbent member 30 and a secondary absorbent member (base member) 50 joined together by union means 70. The primary and secondary absorbent members each have corresponding body facing and garment facing surfaces. As shown in FIG. 1, the compound sanitary napkin 20 has flaps 33 extending from the longitudinal sides of the secondary absorbent member 50 in the central region 28 of the compound sanitary napkin 20.

The primary absorbent member 30 is, as its name implies, that constitute of the compound sanitary napkin 20 intended to absorb the bulk of bodily fluids discharged by the wearer. The primary absorbent member 30 has generally rectangular shape extending in the longitudinal direction along the longitudinal centerline L. The primary absorbent member 30 also has longitudinal sides 24 and transverse ends 25 which together form the periphery 26 of the primary absorbent member 30 and has a longitudinal length PL and a transverse width PW, and a thickness PT. The longitudinal length PL may be generally equal to the longitudinal length SL of the secondary absorbent member 50. The transverse width PW may be generally narrower than the transverse width SW of the secondary absorbent member 50. The primary absorbent member 30 comprises a primary absorbent element such as a primary absorbent core 34, a fluid pervious cover such as fluid pervious topsheet 32 superimposed on the primary absorbent core 34.

The topsheet 32 is preferably compliant, of feeling, and non-irritating to the wearer's skin. Further, the topsheet 32 is fluid pervious, permitting fluid to readily penetrate through its thickness. A suitable topsheet 32 may be manufactured from a wide range of materials such as woven and nonwoven materials; polymeric materials such as apertured formed thermoplastic films, apertured plastic films, and hydroformed thermoplastic films; porous foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers. A preferred topsheet comprises an apertured formed film. Apertured formed films are preferred for the topsheet because they are pervious to body exudates and yet non-absorbent and have a reduced tendency to allow fluids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson, on Dec. 30, 1975; U.S. Pat. No. 4,324,246 issued to Mullane et al., on Apr. 13, 1982; U.S. Pat. No. 4,342,314 issued to Radel, et al., on Aug. 3, 1982; U.S. Pat. No. 4,463,045, issued to Ahr, et al., on Jul. 31, 1984 and U.S. Pat. No. 5,006,394 issued to Baird, on Apr. 9, 1991. Each of these patents are incorporated herein by reference. The preferred topsheet for the primary absorbent member is a formed film described in one or more of the above patents and marketed on sanitary napkins by The Procter & Gamble Company of Cincinnati, Ohio as "DRIWEAVE".

The body or exposed surface of the formed film topsheet may be hydrophilic so as to help fluid transfer through the topsheet faster than if the body surface was not hydrophilic so as to diminish the likelihood that menstrual fluid will flow off the topsheet rather than flowing into and being absorbed by the absorbent core. In a preferred embodiment, surfactant may be incorporated into the polymeric materials of the formed film topsheet such as is described in PCT Publication No. WO93/09741 published on May 23, 1993 in the name of Aziz, et al., which is incorporated herein by reference. Alternatively, the body surface of the topsheet can be made hydrophilic by treating it with a surfactant such as described in U.S. Pat. No. 4,950,264 issued to Osborn, on Aug. 21, 1990 and which is incorporated herein by reference.

Figure 5:
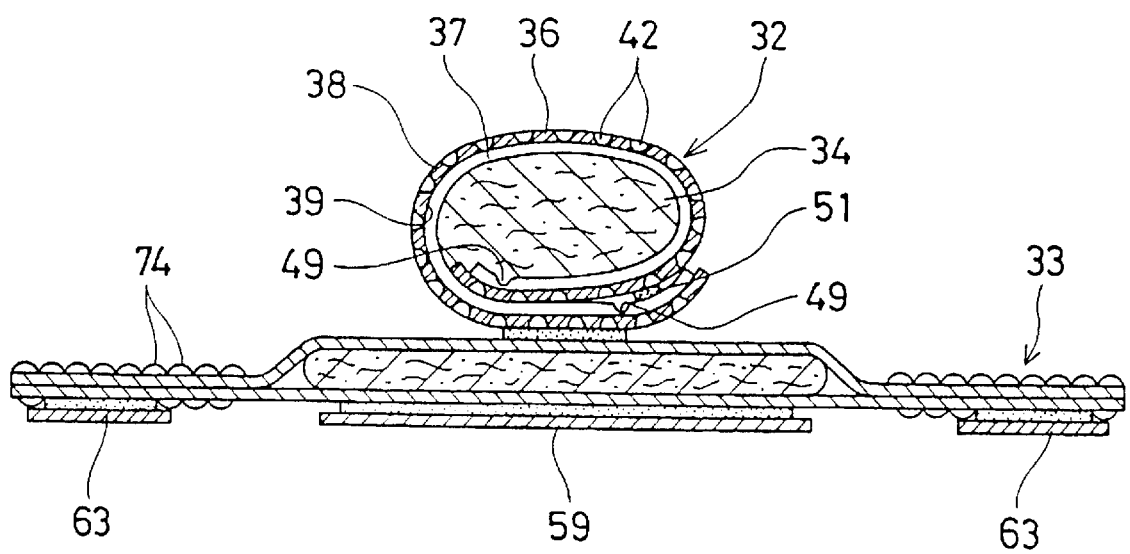
FIG. 5 is a cross-sectional view of another embodiment of the compound sanitary napkin.
Figure 6:
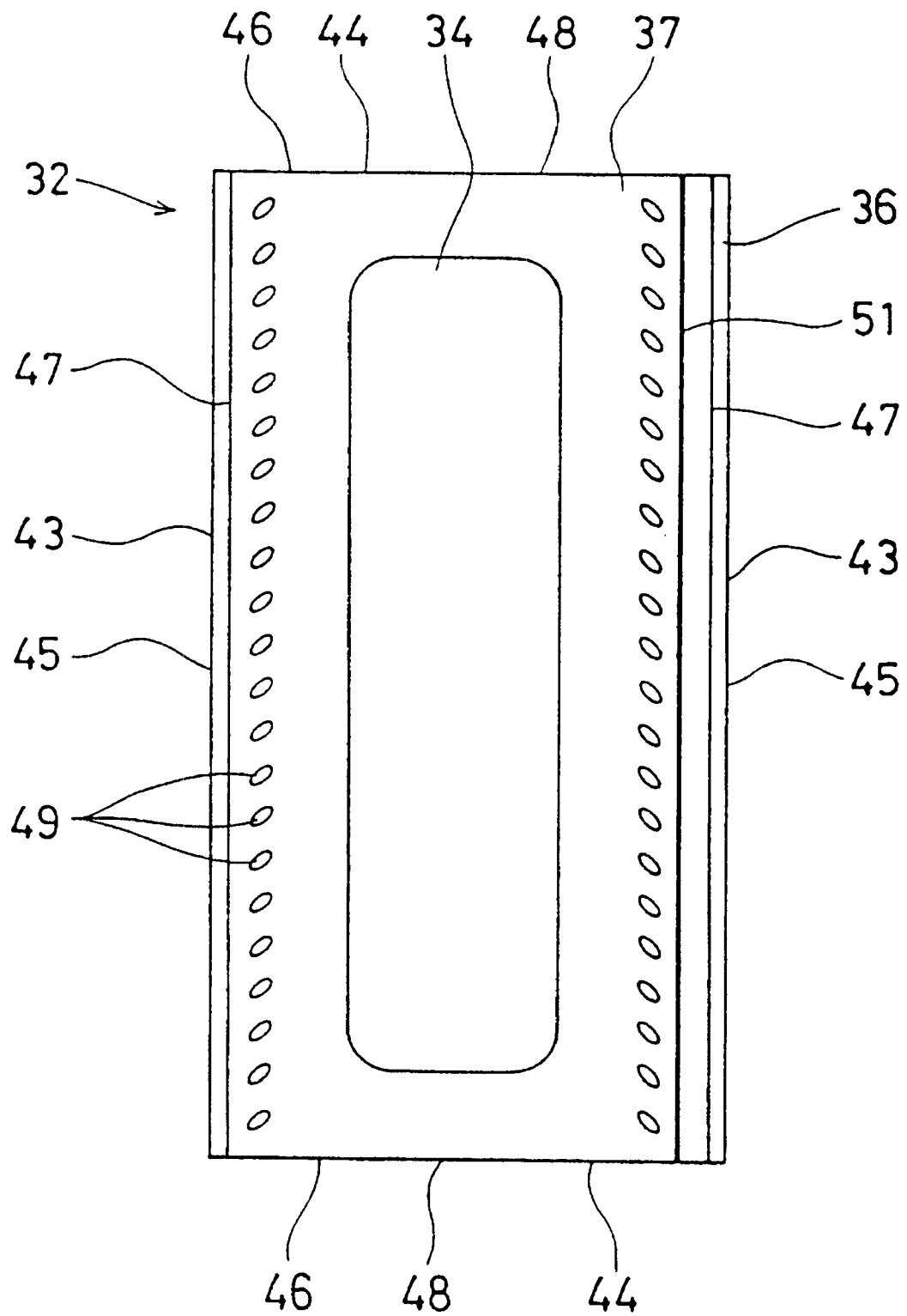
FIG. 6 is a top plan view of a unfolded fluid pervious cover with a primary absorbent element of a primary absorbent member.

In a preferred embodiment, as shown in FIG. 5, the topsheet 32 may comprises a nonwoven 37 and a formed film 36 superposed on the nonwoven 37. The formed film 36 has a first surface 38 facing outwardly, a second surface 39 facing the nonwoven 37 and the primary absorbent core 34, and apertures 42 extending from the first surface 38 to the second surface 39. The area of the apertures 42 in the second surface 39 adjacent to the primary absorbent core 34 is generally smaller than the area of the apertures 42 in the first surface 38. Because the aperture area of the first surface 38 is generally greater than the aperture area of the second surface 39, fluid can easily penetrate the topsheet 32 toward the primary absorbent core 34. However, it inhibits fluid acquired in the primary absorbent core 34 from transferring from the primary absorbent core 34 toward the outside and from rewetting the wearer's skin. The nonwoven 37 is superposed to the second surface 39 of the formed film. The formed film 36 and the nonwoven 37 each has rectangular shape when the formed film 36 and the nonwoven 37 are unfolded as shown in FIG. 6. The topsheet 32 has longitudinal sides 45 and transverse ends 46. The formed film 36 has corresponding longitudinal sides 43 and transverse ends 44 and the nonwoven 37 has corresponding longitudinal sides 47 and the transverse ends 48. The formed film 36 and the nonwoven 37 may be superposed by any suitable manner. Preferably, the formed film 36 and the nonwoven 37 may be joined to one another along the longitudinal sides 45 by a plurality of discrete dots 49. The discrete dots may be formed by applying pressure, heat, pressure and heat, and/or adhesive. Alternatively, the formed film 36 and the nonwoven 37 may be joined to one another along the entire length of the longitudinal sides 45.

The primary absorbent core 34 may be any absorbent means which is generally compressible, conformable, resilient, non-irritating to the wearer's skin and capable of absorbing and containing body. exudates. The primary absorbent core 34 may be manufactured from a wide variety of fluid absorbent materials commonly used in disposable sanitary napkins, and other disposable absorbent articles. Examples of suitable absorbent materials include comminuted wood pulp (which is generally referred to as airfelt), creped cellulose wadding, modified cross-linked cellulose fibers (such as those described in U.S. Pat. No. 5,217,445 issued to Young, et al., on Jun. 8, 1993), capillary channel fibers (that is, fibers having intra-fiber capillary channels such as those described in U.S. Pat. No. 5,200,248 issued to Thompson, et al., on Apr. 6, 1993), absorbent foams (such as those described in U.S. Pat. No. 5,260,345 issued to DesMarais, et al., on Nov. 9, 1993 and U.S. Pat. No. 5,268,244 issued to DesMarais, et al., on Dec. 7, 1993), thermally bonded airlay materials (such as those material described in U.S. Pat. No. 5,607,414 issued to Richards, et al., on Mar. 4, 1997), hydrogel-forming polymer gelling agents (such as those material described in U.S. Pat. No. 4,673,402 issued to Weisman, et al., on Jun. 16, 1987 and U.S. Pat. No. 4,935,022 issued to Lash et al., on Jun. 19, 1990), absorbent sponges, synthetic staple fibers, polymeric fibers, peat moss, or any equivalent materials or combinations of materials. Suitable absorbent cores comprising foams are described in U.S. Pat. No. 5,260,345 issued to DesMarais, et al., on Nov. 9, 1993; U.S. Pat. No. 5,147,345 issued to Young, et al., on Sep. 15, 1992; U.S. Pat No. 5,1949,720 issued to DesMarais, et al., on Sep. 22, 1992; U.S. Pat. No. 5,198,472 issued DesMarais, et al., on Mar. 30, 1993 and U.S. Pat. No. 5,250,576 issued DesMarais, et al., on Oct. 5, 1993. Additional cores comprising foams are described in European Application 0 293 208 B1. Absorbent cores comprising sponges are described in U.S. Pat. Nos. 3,512,530 and 3,954,493 and French Patent 2,203, 827.

Materials selected for use as the primary absorbent core 34 are preferably compliant, soft, comfortable, compressible and resilient to enhance body fit and comfort of the primary absorbent member 30. Preferably, the primary absorbent core 34 is compressible such that the primary absorbent member 30 will deform under relatively small forces that are experienced during normal use. In addition to being compressible, the materials comprising the primary absorbent core 34 are preferably conformable such that the primary absorbent member 30 is able to provide improved fit into and around the labia and perineum. While being generally compressible and conformable under relatively small forces, those forces exerted by the external female genitalia during use, it is also important that the primary absorbent member 30 be sufficiently resilient such that when subjected to normal wearing forces it does not permanently collapse. Preferably, the primary absorbent member 30 will be sufficiently resilient that it will conform to the contours of the body to provide intimate contact with the exposed genitalia of the female use. Intimate contact with the exposed female genitalia helps provide better fluid transfer from the wearer into the primary absorbent member without allowing fluid to bypass and/or run-off the primary absorbent member. While the resilient characteristics of the primary absorbent core 34 allow for improved fit, they must be balanced against the need for the product to be both soft and comfortable for the wearer.

In a preferred embodiment, the primary absorbent core 34 comprises hydrogel-forming polymers and hydrophilic fibers such as airfelt. Preferably, the primary absorbent core 34 comprises hydrogel-forming polymers of between 10% and 60%. More preferably, the primary absorbent core 34 comprises hydrogel-forming polymers of between 15% and 50%. The primary absorbent core 34 may includes airfelt of between 40% and 90%. Preferably, the primary absorbent core 34 may includes airfelt of between 50% and 85%. If necessary, the primary absorbent core 34 may further include hydrophobic fibers. As shown in FIG. 3, the primary absorbent core 34 is manufactured in a generally cylindrical shape to provide the primary absorbent member 30 with a generally cylindrical shape. While the primary absorbent core 34 shown in FIG. 3 has a generally circular cross-section, the absorbent core may be manufactured in a wide variety of shapes such as rectangular, triangular, oval, square, pentagonal, U-shaped, Z-folded, etc.

The topsheet 32 may encircle the primary absorbent core 34 as shown in FIGS. 2 and 3. The topsheet 32 has longer length and wider width than the primary absorbent core 34 (shown in FIG. 6). The transverse width of the topsheet 32 is more than twice of the transverse width of the primary absorbent core 34. This allows the longitudinal sides 45 of the topsheet 32 to overlap underneath the primary absorbent core 34 to encircle the primary absorbent core 34 as shown in FIG. 3. The longitudinal sides 45 of the topsheet 32 may be secured by any suitable manner to keep the encircled shape. Suitable manners include, but are not limited to adhesives such as line adhesive, spiral adhesive, or spot adhesive. In a preferred embodiment shown in FIGS. 3 and 6, line adhesive 51 is applied to one of the longitudinal sides 45 of the topsheet 32 along the entire length of the longitudinal length. Alternatively, intermittent line adhesive may be applied along the entire length of the longitudinal length.

The topsheet 32 may be associated with the primary absorbent core 34 in any suitable manner. Suitable manners include, but are not limited to associating the topsheet 32 with the primary absorbent core 34 with adhesives such as by spray adhesive, line adhesives or spot adhesive between the topsheet 32 and the primary absorbent core 34. Alternatively, or additionally, the topsheet 32 may be associated with the primary absorbent core 34 by entangling the fibers of the primary absorbent core 34 with the topsheet 32, by fusing the topsheet 32 to the primary absorbent core 34 with a plurality of discrete individual fusion bonds, or by any means known in the art. To insure proper fluid transfer between the topsheet 32 and the primary absorbent core 34, it is preferred that the topsheet 32 be substantially continuously secured to the underlying primary absorbent core 34 throughout their common association or interface. By substantially continuously securing the topsheet 32 to the underlying primary absorbent core 34, the topsheet 32 will have a reduced tendency to separate from the primary absorbent core 34 during use. Separation of the absorbent core from the topsheet 32 may inhibit fluid transfer from the topsheet 32 into the underlying primary absorbent core 34. Therefore, the body-facing side of the primary absorbent core 34 may be secured to the topsheet 32 by, i.e., adhesive while the body-facing side of the primary absorbent core 34 may not be secured to the topsheet 32 so as to delay fluid transfer from the primary absorbent core 34 into the secondary absorbent member 50.

The primary absorbent member 30 is preferably circular or oval in cross-section while the primary absorbent member 30 can be generally of any cross-sectional shape in its unstressed condition. The length PL, the width PW and the thickness PT of the primary absorbent member 30 can be of any convenient dimension. The length PL is preferably from about 10 to 35 cm, and more preferably from about 20 to 35 cm. Preferably, the length PL of the primary absorbent member 30 may be generally equal to the length SL of the secondary absorbent member 50. The width PW is preferably from about 0.5 to 5 cm, more preferably from about 1 to about 5 cm, and most preferably from about 2 to about 4 cm. The width PW of the primary absorbent member 30 may be less than the width SW of the secondary absorbent member 50. The thickness PT is preferably from about 0.2 to 2.0 cm, more preferably from about 0.2 to 1.5 cm, and most preferably from about 0.4 to 1.2 cm. Preferably, the thickness PT of the primary absorbent member 30 may be greater than the thickness ST of the secondary absorbent member 50. A ratio of the thickness PT to the width PW, or the ratio (PT/PW) may be between 0.05 and 1.5. Preferably, the ratio may be between 0.08 and 1.00. More preferably, the ratio may be between 0.08 and 0.5.

The caliper of the primary absorbent member 30 is determined by the following test. A comparator gauge, and specifically the Peacock Gage Model No. 307, available from Ozaki Manufacturing Co., LTD. may be used. The comparator gauge should have a circular comparator foot made of aluminum and having a weight of 9.0 grams and a contact surface of 16 square centimeters. The comparator gauge is zeroed. An 60.0 grams stainless steel weight is placed on the spindle extending above the comparator dial. The comparator foot is raised and the primary absorbent member and the primary absorbent member is placed garment surface down on the base plate. The primary absorbent member is positioned on the base plate so that when the foot is lowered it is in the region of the primary absorbent member for which the measurement is desired. Try to smooth out or avoid any wrinkled in the primary absorbent member. Gently lower the foot onto the primary absorbent member. Determine the primary absorbent member caliper by reading the comparator dial 5 to 10 seconds after the foot comes in contact with the primary absorbent member.

The primary absorbent member 30 is preferably relatively conformable. It is preferred to keep the primary absorbent member relatively conformable so that it will readily fit into the labial grove during use. It has been found that a primary absorbent member having the width and/or thickness is able to comfortably fit next to the labial area. While primary absorbent members have been described above as having width or thickness greater than the above width or thickness, they too may fit within the labial groove if they are sufficiently conformable. It is not necessary that all of the primary absorbent member fit within the labial groove, however, a portion of the primary absorbent member is preferably capable of fitting within the labial groove.

The primary absorbent member 30 may include optional elements. The primary absorbent member 30 may optionally comprise a resilient member with the primary absorbent core 34. The resilient member may comprise a single member or a plurality of individual members. Suitable materials which may be used as the resilient member include, but are not limited to, nylon, polypropylene, polyurethane, polyethylene, polyesterm synthetic rubber, and other synthetic materials such as formed films, or natural materials such as rubber, sponges, and the like or any suitable material which is capable of resisting collapse under normal wearing conditions of sanitary napkins during use. The resilient member may be manufactured in a wide variety of shapes such as rectangular, triangular, oval, square, pentagonal, U-shaped, Z-folded, etc. The resilient member may extend throughout the entire length of the primary absorbent member 30. The resilient member may only extend through a portion of the length of the primary absorbent member 30. The resilient member may be positioned within the first end region 27, the central region 28, the second end region 29 or any combination of the above. For example, the resilient member may be positioned in either the first end region 27 or the second end region 29 of the primary absorbent member, in both the first end region 27 and the second end region 29 of the primary absorbent member 30, in the central region 28 of the primary absorbent member, or in the central region 28 and the end regions 27, 29 of the primary absorbent member 30.

Optionally, the primary absorbent member 30 may comprise an acquisition layer positioned between the topsheet 32 and the primary absorbent core 34. The acquisition layer may serve several functions including improving wicking of exudates over and into the primary absorbent core 34. By improving the wicking of exudates, the acquisition layer provides a more even distribution of the exudates throughout the primary absorbent core. The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and PCT Publication No. WO93/11725 published, on Jun. 24, 1993 in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

The second necessary constituent of the compound sanitary napkin 20 is the secondary absorbent member (base member) 50. Referring to FIGS. 1–3, the secondary absorbent member 50 has generally rectangular shape extending in the longitudinal direction along the longitudinal centerline L. The secondary absorbent member 50 also has longitudinal sides 21 and the transverse ends 22 which together form the periphery 23 of the secondary absorbent member 50 and has a longitudinal length SL and a transverse width SW, and a thickness ST. In a preferred embodiment, the longitudinal length SL may be generally equal to the longitudinal length PL of the primary absorbent member 30. The transverse width SW may be generally broader than the transverse width PW of the primary absorbent member 30.

The second absorbent member 50 has two surfaces, a body-contacting surface or "body surface" 50A and a garment surface 50B. The secondary absorbent member 50 is shown in FIG. 1 as viewed from its body surface 50A with the primary absorbent member 30 thereon. The body surface 50A is intended to face the wearer's body when the compound sanitary napkin 20 is worn by interposing the primary absorbent member 30 between the wearers body and the body surface 50A. The garment surface 50B is intended to be placed adjacent to the wearer's undergarments when the compound sanitary napkin 20 is worn. FIG. 1 shows that the secondary absorbent member 50 of the compound sanitary napkin 20 comprises the portion of the secondary absorbent member 50 without the flaps 33. The secondary absorbent member 50 also has two end regions, which are designated first end region 27A and second end region 29A. A central region 28A is disposed between the end regions 27A and 29A. The end regions 27A and 29A extend outwardly in the longitudinal direction from the edges of the central region 28A. As shown in FIGS. 2 and 3, the secondary absorbent member 50 preferably comprises a fluid pervious body-facing sheet or fluid pervious topsheet 52, a fluid impervious garment-facing sheet or fluid impervious backsheet 54 joined with the topsheet 52, and a secondary absorbent element 56 such as a secondary absorbent core 56 positioned between the topsheet 52 and the backsheet 54. The secondary absorbent member 50 may further have a secondary topsheet between the topsheet 52 and the secondary absorbent core 56. The topsheet 52, the backsheet 54, and the absorbent core 56 may be assembled in a variety of configurations known in the art (including layered or "sandwich" configurations and wrapped or "tube" configurations).

FIGS. 1–3 show a preferred embodiment of the secondary absorbent member 50 assembled in a sandwich construction in which the topsheet 52 and the backsheet 54 have length and width dimensions generally larger than those of the secondary absorbent core 56. The topsheet 52 and the backsheet 54 extend beyond the edges of the secondary absorbent core 56 to form portions of the periphery 23. The topsheet 52 is preferably joined to the body-facing side of the secondary absorbent core 56 and the backsheet 54 is preferably joined to the garment-facing side of the secondary absorbent core 56. The topsheet 52 and backsheet 54 can be joined to the secondary absorbent core 56 in any suitable manner known in the art for this purpose, such as by an open pattern of adhesives. If the secondary absorbent member 50 has the secondary topsheet, the topsheet 52 may be joined to the secondary topsheet and the secondary topsheet may be joined to the absorbent core 56. This joint of each layer increases integrity of the secondary absorbent member 50. The portions of the topsheet 52 and backsheet 54 that extend beyond the edges of the secondary absorbent core 56 are preferably also joined to each other. The topsheet 52 and backsheet 54 can be joined in any suitable manner known in the art for this purpose. Preferably, in the embodiment shown, these portions of the topsheet 52 and backsheet 54 are preferably joined using adhesives over substantially the entire portions that extend beyond the edges of the secondary absorbent core 56, and/or a crimp seal at the transverse ends 22 of the secondary absorbent member 50 where the topsheet 52 and backsheet 54 are densified by the application of pressure or heat and pressure.

The topsheet 52 can be any fluid pervious material commonly used in sanitary napkins, disposable diapers, and the like. It can be any of the materials described above as being useful in the topsheet 32 of the primary absorbent member 30. A preferred topsheet 52 comprises an apertured formed film. Apertured formed films are preferred for the topsheet because they are pervious to body exudates and yet non-absorbent and have a reduced tendency to allow fluids to pass back through and re-wet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson, on Dec. 30, 1975; U.S. Pat. No. 4,324,246 issued to Mullane, et al., on Apr. 13, 1982; U.S. Pat. No. 4,342,314, issued to Radel, et al., on Aug. 3, 1982; U.S. Pat. No. 4,463,045 issued to Ahr, et al., on Jul. 31, 1984 and U.S. Pat. No. 5,006,394 issued to Baird, on Apr. 9, 1991. Each of these patents are incorporated herein by reference. The preferred topsheet for the primary absorbent member is a formed film described in one or more of the above patents and marketed on sanitary napkins by The Procter & Gamble Company of Cincinnati, Ohio as "DRI-WEAVE".

The secondary absorbent core 56 can be any absorbent material commonly used in sanitary napkins, disposable diapers and the like. It can be any of the materials described above as being useful in the primary absorbent core 34 of the primary absorbent member 30. As a practical matter, most of the bodily fluids are absorbed by and are contained within the primary absorbent core 34 of the primary absorbent member 30. One major function of the secondary absorbent member 50 is to protect the wearer'undergarments from soiling by absorbed fluids which may be expelled from the primary absorbent member 30 or which may inadvertently bypass the primary absorbent member 30. The overall absorptive capacity of the secondary absorbent core 56 may be, therefore, somewhat less than that of the primary absorbent core 34. Because the primary absorbent core 34 is preferably intended to absorb most or substantially all of the bodily fluids during use, its absorptive capacity will be somewhat if not significantly greater than that of the secondary absorbent core 56. Because the secondary absorbent core 56 performs a different function from that of the primary absorbent core 34, the secondary absorbent core 56 can be, and most preferably is, somewhat thinner and less bulky than the primary absorbent core 34.

Because the secondary absorbent core 56 has different requirements than does the primary absorbent core 34, it can be formed of different materials. For example, single or multiple plies of paper tissue as commonly used in paper toweling or toilet tissue can be used to form the secondary absorbent core 56. Preferably, the secondary absorbent core 56 is formed of from about 1 to about 5 plies of paper tissue. Paper tissue comprising one or more plies having a basis weight of from about 24 to about 48 grams per square meter and an apparent density of from about 0.10 to about 0.12 grams per cubic centimeter as made by the process described in U.S. Pat. No. 3,301,746 issued to Sanford and Sisson, on Jan. 31, 1967 and which patent is hereby incorporated herein by reference has been found to be quite satisfactory for use as the secondary absorbent core 56. Wet strength resins and latex binders can be, and preferably are, used to provide additional strength to the paper tissue used in the absorbent core. Paper tissue made by the process described in U.S. Pat. No. 3,994,771 issued to Morgan et al., on Nov. 30, 1976, and which patent is hereby incorporated herein by reference, can also be used to good advantage as the secondary absorbent core 56.

The secondary absorbent core 56 may have any suitable shape including, but are not limited to, oval, hourglass, dog-bone, asymmetric, etc. In a preferred embodiment shown in FIG. 1, the secondary absorbent core 56 has generally rectangle shape encompassed by longitudinal sides 55 and transverse edges 57. The secondary absorbent core 56 also has a longitudinal length CL, a transverse width CW and a thickness CT. The longitudinal length CL may be shorter than the longitudinal length PL and SL. The length CL may be from about 10 to about 33 cm, preferably from about 15 to about 33 cm. The transverse width CW may be wider than the transverse width PW of the primary absorbent member 30 at least in the central region 28A (i.e., the crotch region corresponding to the crotch region of the undergarment when the compound sanitary napkin is used). More preferably, the transverse width CW may be wider than the transverse width PW of the primary absorbent member 30 throughout the entire length. The width CW may be from about 3 to about 12 cm, preferably from about 4 to about 10 cm, more preferably from about 5 to about 8 cm.

The backsheet 54 is impervious to fluids (e.g., menses and/or urine) and is preferably manufactured from a thin plastic film, although other flexible fluid impervious materials may also be used. As used herein, the term "flexible" refers to materials which are compliant and will readily conform to the general shape and contours of the human body. In use, the backsheet 54 is interposed between the secondary absorbent core 56 and the wearer's undergarments. The function of the backsheet 54 is to prevent exudates which may be expelled from or which inadvertently bypass the primary absorbent core 30 and exudates absorbed and contained in the secondary absorbent core 56 from contacting and soiling the wearer's undergarments. The backsheet 54 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm(0.5 mil) to about 0.015 mm (2.0 mil). Exemplary polyethylene films are manufactured by Clopay Corporation of Cincinnati, Ohio under the designation P18-0401 and by Ethyl Corporation, Visqueen Division, of Terre Haute, Ind., under the designation XP-39385. The backsheet is preferably embossed and/or matte finished to provide a more cloth like appearance. Further, the backsheet may permit vapors to escape from the absorbent core 56 (i.e., breathable) while still preventing exudates from passing through the backsheet 54.

The shape of the secondary absorbent member 50 can be of generally rectangular encompassed by the longitudinal sides 21 and the transverse ends 22. Other suitable shapes include but are not limited to oval, hourglass, dog-bone, asymmetric, etc.

The compound sanitary napkin 20 shown in FIGS. 1–4 also comprises a pair of flaps 33 that are joined to the secondary absorbent member 50. The flaps 33 extend laterally outward beyond the longitudinal sides 21 of the secondary absorbent member 50 from their proximal edges 40 to their distal edges (or "free end") 41. The flaps 33 extend outward from at least the central region 28A of the secondary absorbent member 50. As shown in FIG. 1, each flap 33 is divided into a front half 60, and a back half 61 by a flap transverse centerline $T_1$. The lap transverse centerline $T_1$ may coincide with the principal transverse centerline of the sanitary napkin, but this is not absolutely required. The flaps 33 are provided with flap fasteners or adhesive attachment means 62 to secure the flaps 33 to the wearer's undergarment.

The flaps 33 can be joined to the secondary absorbent member 50 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIGS. 1–4, the flaps 33 are integral with the secondary absorbent member 50 (that is, the flaps 33 comprise integral extensions of the topsheet 52 and backsheet 54).

In other alternative embodiments, the flaps 33 can comprise one or more separate components that are joined to the garment-facing side of the secondary absorbent member 50. Preferably, in such a case, the flaps 33 each comprise a separate component that is joined to the garment-facing side of the secondary absorbent member 50. In such alternative embodiments, the flaps 33 are preferably otherwise unattached to the garment-facing side of the secondary absorbent member 50 of the compound sanitary napkin 20 between the points where they are attached to the secondary absorbent member 50 and the longitudinal sides 26 of the secondary absorbent member 50. The flaps 33 in these latter embodiments can be joined to the garment-facing side of the secondary absorbent member 50 by any suitable attachment mechanism. Suitable attachment mechanisms include, but are not limited to adhesives, and the like.

The flaps 33 are each joined to (or associated with) secondary absorbent member 50 along a juncture. This is typically a longitudinally-oriented (or "longitudinal") juncture, such as lines of juncture 31. As used herein, the terms "juncture" (or "line of juncture") refer to regions where the flaps 33 extend from or are joined to the secondary absorbent member 50. These regions can be any of various curved or straight lines, but they are not limited to lines. Thus, these regions can comprise flanges, strips, intermittent lines, and the like. The line of juncture 31 in the embodiment illustrated in FIG. 1 can be considered to be defined by concave inwardly-oriented regions or lines if the proximal edges 40 of the flaps 33 are considered to coincide with the inwardmost boundary of the hinge 65 (described below). In the preferred embodiment shown in FIG. 1, the entire length of the juncture 31 may be not less than 20% of the entire length of the primary absorbent member 30. More preferably, the entire length of the juncture 31 may be not less than 25% of the entire length of the primary absorbent member 30. Therefore, if the juncture 31 coincid with the proximal edge 40 of the flaps 33, the entire length of the proximal edge 40 may be not less than 20%, more preferably not less than 25% of the primary absorbent member 30. The compound sanitary napkin 20 having the juncture 31 of not less than 20% of the entire length of the primary absorbent member 30 allows the compound sanitary napkin 20 to make a wider coverage for the leg openings of the wearer's undergarment and to stay in a right place in the wearer's undergarment by the holding function of the flaps 33 having relatively longer juncture 31. Thereby, the compound sanitary napkin 20 also allows the primary absorbent member 30 to stay adjacent to the wearer's body where the exudates which are discharged from the body are expected.

The compound sanitary napkin 20 shown in FIGS. 1–4 preferably has a hinge 65 between the secondary absorbent member 50 and at least a portion of the flaps 33. The secondary absorbent member 50 of the compound sanitary napkin 20 preferably also has at least one zone of extensibility (or "zone of differential extensibility") 66 for relieving the stresses on the flaps 33 when they are folded around a undergarment crotch. These are each described below.

In the sanitary napkin shown in FIGS. 1–4, the hinge 65 preferably comprises a generally longitudinally-oriented, mechanically-deformed region. The hinge 65 provides a region of the secondary absorbent member 50 with increased flexibility to create preferred bending axes for the flaps 33 to bend or fold about. The hinge 65 is preferably located in a region along the juncture 31 of the flaps 33 with the secondary absorbent member 50. The hinge 65, however, does not have to coincide exactly with the juncture 31 of the flaps 33 with the secondary absorbent member 50. The hinge 65 can be located laterally inboard of the juncture 31 of the flaps with the secondary absorbent member 50, on the juncture, laterally outboard of the juncture, or any combination of the foregoing. If the hinge 65 is located laterally inboard of the juncture or on the juncture, the hinge 65 may be considered to be formed in at least part of the secondary absorbent member 50 (and, in the latter case, also in part of the flaps 33).

The hinge 65 can extend along the entire juncture 31 of the flaps with the secondary absorbent member, or along only a portion thereof. If the hinge 65 is only provided along a portion of the juncture 31, it is preferably provided in the region of the sanitary napkin 20 surrounding and including the flap transverse centerline. The hinge 65 can be in many possible configurations. The hinge 65 can comprise a continuous region, or a plurality of spaced apart intermittent regions. The hinge 65 can be rectilinear, curvilinear, or it can comprise portions that are rectilinear and portions that are curvilinear. The hinge 65 has a laterally inwardmost, or proximal, boundary 65A and an outermost, or distal, boundary 65B. In the embodiment shown in FIGS. 1–4, at least the inwardmost boundary 65A of the hinge 65 is preferably concave inwardly relative to the distal edge of the flaps 54.

The hinge 65 can be formed in any suitable manner that provides the desired region of the sanitary napkin with increased flexibility. Preferably, the hinge 65 is formed by mechanically deforming the desired regions of the secondary absorbent member. It has been found that many processes suitable for providing regions of the secondary absorbent member with extensibility are particularly suitable for providing regions of the secondary absorbent member 50 selected for the hinge 65 with enhanced flexibility.

The hinge 65 can, for instance, be formed by a process which has been described as pre-corrugating (or "ring rolling"). Suitable methods for ring rolling are described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

Alternatively, as shown in FIG. 1 for purposes of illustration, the hinge 65 is provided by forming a strainable network in the region along the juncture 31 of the flaps 33 with the secondary absorbent member 50. The process for forming a strainable network region, and structures formed thereby are described in greater detail below in conjunction with FIGS. 7–10. This technology is further described in allowed U.S. patent application Ser. No. 08/203,087 filed in the name of Chappell, et al. on Feb. 28, 1994 (PCT Publication No. WO 95/03765, published Feb. 9, 1995).

These structures (ring rolled structures and materials with strainable network regions formed therein) are especially preferred for the hinge 65 because the alternating ridges and valleys can form a plurality of flexible bending axes for the flaps 33. These types of structures also provide the hinge 65 with a degree of extensibility. The extensibility allows the portions of the flaps 33 in the hinge region 65 to expand slightly in the transverse direction to better fold around the curved sides of the wearer's undergarment crotch. Providing the hinge 65 by forming strainable network regions in the secondary absorbent member 50 may also be preferred when it is desired to provide the formed regions with slightly more integrity so the flaps 33 will be less likely to droop excessively at the hinge 65 because the unformed first regions or less extensible bands 84 (described below) of the strainable network will serve like "beams" that tend to provide the flaps 33 with slightly more structural rigidity and better appearance.

The process of forming a strainable network is preferred for providing the secondary absorbent member 50 with a hinge 65 because (like ring rolling) such an operation can be readily adapted for use in high speed manufacturing operations. Further, the process of forming a strainable network in a material is highly preferred because it can be adapted to produce a virtually unlimited number of patterns to tailor the configuration and characteristics of the hinge 65 and zones of extensibility 66.

Typically, the base material into which the strainable network is formed comprises a single layer of material or laminate of materials, at least one of which is a film. Preferably, in the embodiment shown in FIGS. 1–4, the material that has the stainable network formed therein comprises a laminate formed by an extension of the topsheet 52 and backsheet 54 of the secondary absorbent member 50.

Figure 7:
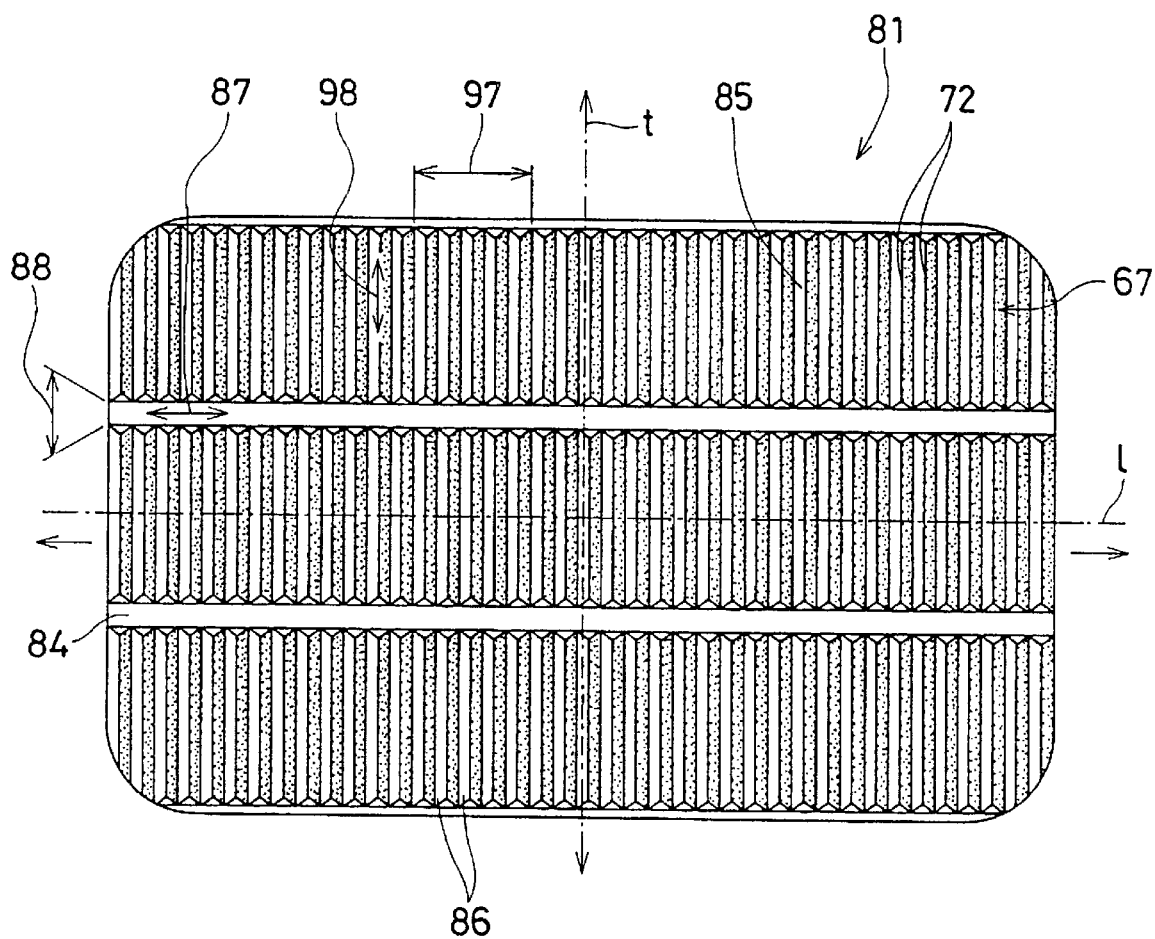
FIG. 7 is a top plan view of a preferred web material having a strainable network of the type used in the deformed hinge of the compound sanitary napkin shown in FIG. 1, the web material being shown in a substantially untensioned condition.
Figure 8:
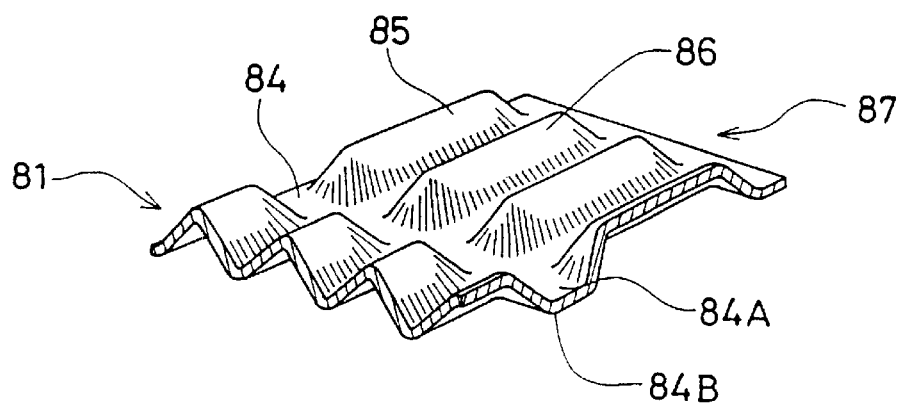
FIG. 8 is an enlarged segmented perspective illustration of the web material shown in FIG. 7 in which the web material is in a substantially untensioned condition.

The characteristics of the strainable network 67 in the hinge 65 of the sanitary napkin shown in FIGS. 1–4 will be discussed with reference to FIGS. 7–10. FIGS. 7–10 are enlarged views of a simplified version of a web material 81 having a strainable network 67 formed therein. The term "strainable network", as used herein, refers to an interconnected and interrelated group of regions which are able to be extended to some useful degree in a predetermined direction. FIGS. 7 and 8 show the web material 81 in an untensioned condition. The strainable network 67 comprises at least two distinct and dissimilar regions which are designated as first region 84 and second region 85.

In the simplified embodiment shown in FIGS. 7 and 8, the web material 81 includes a plurality of first regions 84 and a plurality of second regions 85. As shown in FIGS. 7 and 8, the first regions 84 are substantially planar regions. That is, the material within the first region 84 is in substantially the same condition before and after the formation step undergone by web material 81. The second regions 85 include a plurality of continuous, interconnected, rib-like deformations 86 which extend alternately beyond the plane of both the first and second surfaces (84A and 84B, respectively) of the first region 84. In other embodiments, the deformations 86 may extend beyond the plane of only one of the first 84A or the second 84B surfaces of the first region 84.

FIG. 7 shows that the web material 81 having the strainable network 67 formed therein has a longitudinal centerline (or axis), I, and a lateral centerline (or axis), t. In the sanitary napkin embodiment shown in FIG. 1, the longitudinal centerline, I, of the strainable network 67 is shown as being rectilinear and generally oriented in the transverse direction. However, the longitudinal centerline, I, is not limited to such a configuration and orientation. The longitudinal centerline, I, can be rectilinear, curvilinear, or partially rectilinear and partially curvilinear. The longitudinal centerline, I, of the strainable network 67 can also be oriented in other directions, if desired.

FIG. 7 shows that the first regions 84 of the strainable network 67 have a first axis 87 and a second axis 88, wherein the first axis 87 is preferably longer than the second axis 88. In the simplified embodiment shown, the first axis 87 of the first region 84 is substantially parallel to the longitudinal axis, I, of the web material 81 while the second axis 88 is substantially parallel to the transverse axis, t, of the web material 81. The second regions 85 of the strainable network 67 also have a first axis 97 and a second axis 98. The first axis 97 of the second region 85 is substantially parallel to the longitudinal axis I of the web material 81, while the second axis 98 is substantially parallel to the transverse axis t of the web material 81. In the version of the web material shown in FIGS. 7 and 8, the first regions 84 and the second regions 85 are substantially linear, extending continuously in a direction substantially parallel to the longitudinal axis I of the strainable web material. In other embodiments, the second regions 85 can be curvilinear, or partially rectilinear and partially curvilinear.

Figure 9:
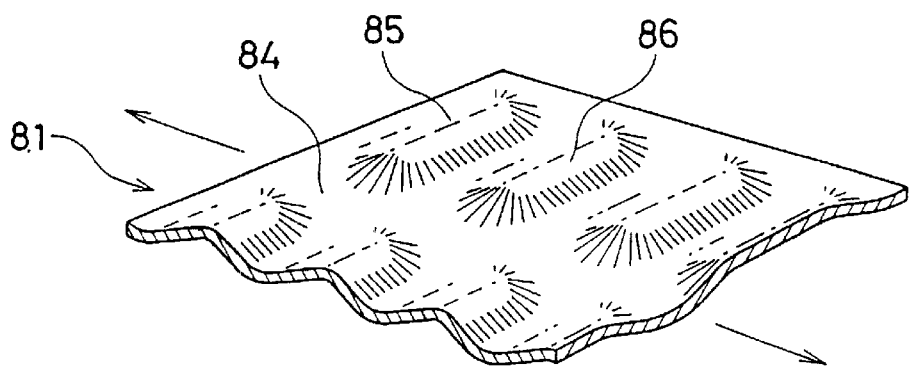
FIG. 9 is an enlarged segmented perspective illustration of the web material shown in FIG. 7 in which the web material is subjected to tension in an amount which is sufficient for a substantial portion of the deformations of the web material to enter the plane of the applied elongation.
Figure 10:
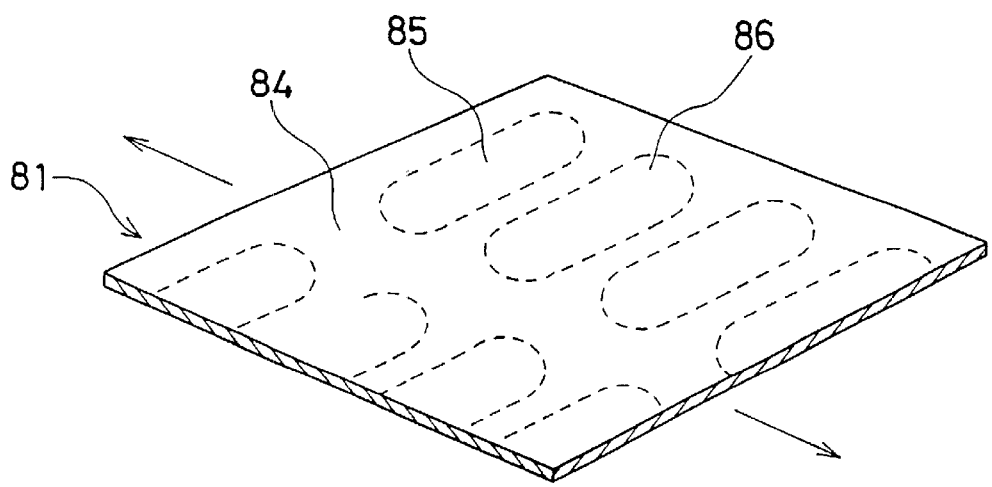
FIG. 10 is an enlarged segmented perspective illustration of the web material shown in FIG. 7 in which the web material is in a condition in which it will exhibit a second stage of resistive forces to elongation.

While the enhanced flexibility of the strainable network is of primary interest in forming the hinge 65, the strainable network also provides portions of the flaps 33 with a degree of extensibility. FIGS. 8–10 show the manner in which the web material 81 with a strainable network 67 formed therein may exhibit at least two significantly different stages of controlled resistive force to elongation when subjected to an applied elongation in a direction parallel to a predetermined axis. The strainable network 67 exhibits first resistive forces to the applied elongation (which develop between the stage shown in FIG. 8 and the stage shown in FIG. 9). The first resistive forces occur until the elongation of the web is sufficient to cause a substantial portion of the second regions 85 to enter the plane of applied elongation, as shown in FIG. 9. After the web material 81 reaches the stage shown in FIG. 9, it exhibits second resistive forces to further elongation (as illustrated by FIG. 10). Typically, when used in regions of the secondary absorbent member 50 described herein, the web material will be within the first stage of resistance to elongation so the various portions of the strainable network 67 will only extend to the stage shown in FIG. 9 and adjust so as to relax back to the stage shown in FIG. 8.

The hinge 65 is created by forming the strainable network 67 into the desired portion of the secondary absorbent member 50. As used herein, the term "forming" refers to the creation of a desired structure or geometry upon a web material or laminate that will substantially retain the desired structure or geometry when it is not subjected to any externally applied elongations or forces. Suitable methods for forming a strainable network into a web material include, but are not limited to embossing by mating plates or rolls, thermoforming, high pressure hydraulic forming, and casting.

The portion of the secondary absorbent member 50 into which the strainable network 67 is formed can comprise a base material (or laminate) that has a relatively low extensibility under the forces that the compound sanitary napkin is normally subjected to when worn. When the strainable network 67 is formed therein, however, the base material can be made extensible under pre-selected forces such as those that the sanitary napkin is normally subjected to when worn.

The depth and number of deformations 86 in the strainable network 67 can be varied to control the applied force or elongation required to extend the material in the hinge regions 65 of the secondary absorbent member 50. In one embodiment, the deformations 86 may be formed by two rigid plates having a pattern of meshing teeth. The outer dimensions of the pattern of teeth covers a surface area of the plates that is about 7.9" by 1.6" (20 cm by 4 cm) for each flap. On one surface of each plate are a series of teeth which are substantially triangular in cross section and taper to a radiused vertex. The teeth in this embodiment preferably have a height of 3.175 mm, and are evenly spaced with the centerlines of the teeth spaced apart at 0.075" (1.9 mm) increments. On the "toothed" side of one plate, a series of grooves (preferably three grooves to construct the embodiment shown in FIG. 1) are cut which are parallel to each other and perpendicular to the evenly spaced teeth. These grooves correspond to the undeformed regions of the base material.

The preferred base material is placed between the plates in a hydraulic press having platens larger than the plates to evenly distribute pressure. The plates are compressed so that the teeth only partially engage (or mesh). Preferably, the plates are moved so that the teeth on the opposite plates are pressed toward each other about 80% of the distance toward full engagement (the point where the teeth would otherwise touch). Typically, in order to do this, when the base material comprises a laminate of apertured formed film and polyethylene backsheet material laminated together by adhesives that is described in conjunction with the embodiment shown in FIGS. 1–4, the plates will be compressed under a load of between about 25–70 psi. (about 1,750–4,900 g/cm2). The formed web material is then removed from between the plates. In the embodiment shown in FIGS. 1–4, the formed web material is provided with about 75% extensibility. The available stretch or elongation is increased if for a given number of deformations, the height or degree of deformation imparted to the web material is increased. Similarly, the available stretch or elongation is increased if for a given height or degree of deformation, the number or frequency of deformations is increased. The mating plates can be configured to create any of the patterns for the hinge 65 on the sanitary napkins shown in the drawings.

The secondary absorbent member 50 also has zones of extensibility 66 for relieving the stresses that develop in the flaps when they are folded down and under the wearer's undergarment and when at least a portion of the primary absorbent member 30 shifts away from the flaps 33. The terms "zone of extensiblity" or "zone of differential extensibility", as used herein, refer to a portion of the secondary absorbent member 50 of the compound sanitary napkin 20 which is capable of extending (and are preferably capable of extending a greater amount than surrounding portions of the secondary absorbent member 50). The secondary absorbent member 50 preferably has at least one zone of extensibility 66 for each flap 33, and more preferably has four zones of extensibility 66. Since the zones of differential extensibility 66 relieve stresses in the flaps, they may be referred to herein as a type of "stress relief means".

The zones of extensibility 66 can be extensible in any desired direction, or in more than one direction. However, the zones of extensibility 66 are preferably primarily extensible generally outward in the transverse direction. As used herein, "generally in the transverse direction" means that the extensibility has a transverse component. In the embodiment shown in FIG. 1, this is generally in the direction of the arrows which is generally at a right angle with the longitudinal direction of the primary absorbent member 30. Alternatively, the zones of extensibility 66 are primarily extensible at an angle with the longitudinal direction of the primary absorbent member 30. All of the extension need not be exactly oriented in the same direction. The extensibility, however, is preferably oriented more in the transverse direction than in the longitudinal direction.

Preferably, the zones of extensibility 66 are extensible at least in the same direction that the primary absorbent member 30 may shift. The zones of extensibility 66 also preferably has sufficient extensibility being capable of a stress given to the flap. Preferably, the zones of extensibility 66 may have extensibility of at least 20% compared with its original length. More preferably, the zones of extensibility 66 may have extensibility of at least 25%. The zones of extensibility is extensible to be capable of a stress given to the flap when the compound sanitary napkin 20 is worn. The flaps 33 are also substantially free from shifting when a portion of the primary absorbent member 30 shifts away from the flap 33. Namely, when the compound sanitary napkin 20 is worn and the wearer moves, e.g., walks, a portion of the primary absorbent member 30 may shift. For example, the transverse end 25 of the primary absorbent member 30 may shift away from the flap when the primary absorbent member 30 shifts with the wearer's body. Since the flap is secured to the undergarment by the adhesive attachment means 62, such a shift of the primary absorbent member 30 may give a stress to the flap 33. However, since the flaps 33 are substantially free from shifting when a portion of the primary absorbent member 30 shifts away from the flap 33, the flaps 33 can keep staying on the undergarment without detaching therefrom.

The zones of extensibility 66 can comprise any structure capable of extending in the transverse direction (or in any other direction desired). The extensibility referred to herein may be preferably elasticless. That is, it may be accomplished without the use of separate elastic pieces, strands, or materials to contract one or more portions of the sanitary napkin. Alternatively, it may be accomplished with the use of separate elastic pieces, strands, or materials to contract one or more portions of the sanitary napkin. The zones of extensibility may also be accomplished without slitting or notching portions of the sanitary napkin that cover the wearer's undergarments. The zones of extensibility 66, therefore, comprise continuous material. This will have the advantage that exudates will not be able to travel through the slits or notches to soil the wearer's undergarments. Alternatively, it may be accomplished with slitting or notching portions of the sanitary napkin that cover the wearer's undergarments.

Suitable structures for the zones of extensibility 66 include, but are not limited to zones of material that are mechanically strained, corrugated, "ring rolled", formed with a strainable network therein, formed with a network of corrugations without any less extensible bands therein, folded, pleated, or joined along a curved juncture. These structures (although shown only as being part of the flaps 33), can comprise portions of the secondary absorbent member 50, portions of the flaps 33, or both. They can be integral parts of these components of the sanitary napkin, or separate elements, such as pieces of material, joined to the sanitary napkin. Suitable structures for the zones of extensibility are described in greater detail in U.S. Pat. No. 5,389,094 issued to Lavash, et al. on Feb. 14, 1995.

In the embodiment shown in FIG. 1, the zones of extensibility 66 can either comprise ring rolled regions of the flaps or a network of corrugations without any less extensible bands therein. In either case, the zones of extensibility 66 preferably have corrugations with ridges that are oriented generally in the longitudinal direction of the primary absorbent member 30 so that the zones of extensibility will be extensible primarily in the transverse direction which is generally at a right angle with the direction where the primary absorbent member 30 extends. Alternatively, the ridges may be oriented generally at an angle with the longitudinal direction of the primary absorbent member 30.

There are many possible arrangements and configurations that the zones of extensibility 66 may have relative to each other and relative to the hinges 65. The zones of extensibility 66 (or at least portions thereof are preferably spaced longitudinally away from the flap transverse centerline T1. As shown in FIG. 1, the portions of the zones of extensibility 66 that are spaced laterally furthest outward from the juncture 31 of the flaps 33 with the secondary absorbent member 50 are separated by an intermediate region 68. The portions of the zones of extensibility 66 that are closest to the juncture 31 of the flaps 33 with the secondary absorbent member 50 can also be spaced longitudinally away from the flap transverse centerline T1 so that they do not abut each other. Alternatively, these portions of the zones of extensibility 66 can abut each other.

The intermediate region 68 comprises a region of the flap 33 that includes the flap transverse centerline T1 and laterally adjacent regions. The intermediate region 68 is preferably stiffer than the regions of the sanitary napkin that comprise the hinge 65 and the zones of extensibility 66. This provides the flaps 33 with more integrity so that they will be easier for the wearer to handle. Thus, the secondary absorbent member 50 of the sanitary napkin is preferably the stiffest portion of the sanitary napkin. The intermediate region 68 is preferably the stiffest portion of the flaps 33, and is preferably not as stiff as the secondary absorbent member 50. The hinge 65 is preferably more flexible than either of those portions of the sanitary napkin. The compound sanitary napkin 20 having the juncture 31 of not less than 20% of the entire length of the primary absorbent member 30 gives the compound sanitary napkin 20 bigger (longer) flaps and bigger intermediate region 68. The bigger intermediate region 68 allows the compound sanitary napkin 20 to have the bigger (or longer) adhesive attachment means 62. Such bigger adhesive attachment means 62 is useful to keep the flaps staying on the desired position on the wearer's undergarment.

The zones of extensibility 66 can be spaced away from the hinge 65, or be adjacent to the hinge 65. Preferably, as shown in FIG. 1, the hinge 65 is contiguous (that is, touching or connected throughout in an unbroken sequence) with the zones of extensibility 66. The hinge 65 and the preferred ring rolled zones of extensibility 66 are, thus, portions of a continuous composite deformed region. As shown in FIG. 1, the hinge 65 gradually transitions into portions of the secondary absorbent member 50 that comprise the zones of extensibility 66. The composite deformed region, thus, comprises continuous corrugations having ridges that are generally oriented in the longitudinal direction with a plurality of inextensible bands 84 in the center region adjacent the flap transverse centerline T1.

Figure 13:
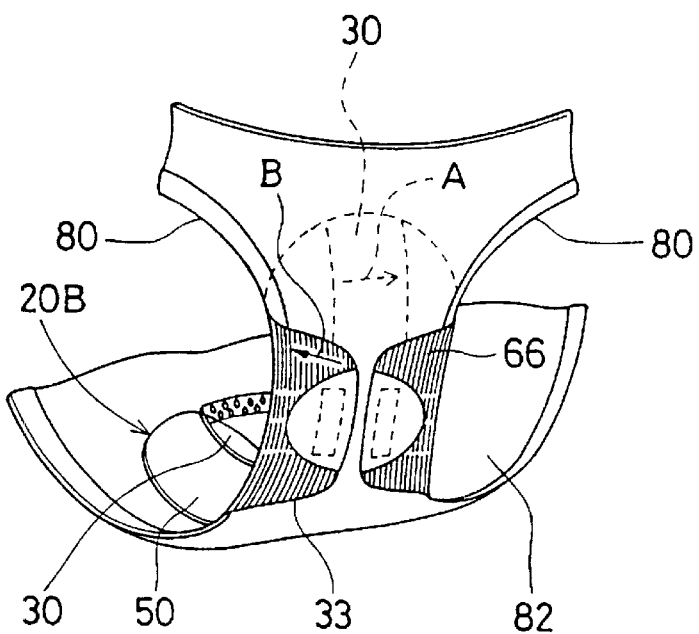
FIG. 13 is a perspective view of the crotch portion of a women's undergarment with the compound sanitary napkin shown in FIG. 1.

As shown in FIG. 1, the composite deformed region preferably has a proximal boundary along the juncture 31 of the flaps 33 with the secondary absorbent member 50 that is concave relative to the proximal edges 40 of the flaps 33. The composite deformed region preferably has a distal boundary that is also concave relative to the distal edges 46 of the flaps 33. FIG. 1 shows that the distal boundary of the composite deformed region defines the boundary of the intermediate region 68 as a generally semi-circular area. Further, as shown in FIG. 1, the radius of curvature of the distal boundary of the composite deformed region is preferably less than the radius of curvature of the proximal edge of the composite deformed region. This is believed to provide the flaps 33 with a smooth fold line around the sides of the crotch of the wearer's undergarment when the compoundsanitary napkin 20 is in place therein (as shown in FIG. 13).

Many variations of the embodiments described herein are possible. For example, instead of comprising corrugations with linear ridges that are oriented in the longitudinal direction, the deformations forming these regions can be arranged in the form of a series of concentric concave ridges and valleys that are aligned with the boundaries of these regions. Alternatively, the hinge 65 and/or the zones of extensibility 66, instead of comprising deformed regions of the sanitary napkin, can comprise some other suitable type of structure that provides the secondary absorbent member 50 with the desired properties of increased flexibility and extensibility in these regions.

The garment surface 20B of the compound sanitary napkin 20 may include, and preferably does include, fasteners for attaching the sanitary napkin to the wearer's undergarment. FIG. 1 shows the central pad fastener 58 which is adapted to secure the secondary absorbent member 50 of the compound sanitary napkin 20 to the crotch region of an undergarment. Any types of fasteners known in the art, such as adhesive fasteners and mechanical fasteners can be used. Fasteners comprising adhesives have been found to work well for this purpose, with pressure-sensitive adhesives being preferred.

The outer surface of the flaps 33, adjacent the distal edges 41 of the flaps, is preferably provided with a flap fastener such as flap adhesive 62. The flap adhesive 62 is used to assist in maintaining the flaps 33 in position after they are wrapped around the edge of the crotch portion of the undergarment. Suitable adhesive fasteners are described in greater detail in U.S. Pat. No. 4,917,697. The flaps 33 can be maintained in position by attaching the flaps 33 to the undergarment, or to the opposing flap.

The fasteners used with the present invention are not limited to adhesive attachment means. Any type of fastener used in the art can be used for such purpose. For example, the compound sanitary napkin 20 could be secured to the wearer's undergarment by mechanical fasteners, such as VELCRO, or the fasteners described in U.S. Pat. No. 4,946,527 entitled "Pressure-Sensitive Adhesive Fastener and Method of Making the Same" issued to Battrell on Aug. 7, 1990, or U.S. Pat. No. 5,392,498 entitled "Non-Abrasive Skin Friendly Mechanical Fastening System" issued to Goulait, et al. on Feb. 28, 1995. For simplicity, however, the fasteners will be described in terms of adhesive attachment means.

The adhesive attachment means are respectively covered by removable release liners, central pad release liner and flap release liner, 59 and 63. The pressure-sensitive adhesives should be covered with release liners 59 and 63 to keep the adhesives from sticking to extraneous surfaces prior to use. Suitable release liners are described in U.S. Pat. No. 4,917, 697. A particularly preferred release liner which also serves as an individual package for wrapping the sanitary napkin is described in U.S. Pat. No. 4,556,146 issued to Swanson, et al. In other embodiments, the flaps 33 could be folded and tucked as described in U.S. Pat. No. 5,281,209 issued to Osborn, et al. on Jan. 25, 1994. The adhesive attachment means on such flaps could, instead of being covered with a release liner, be releasably adhered to a release surface provided on some other portion of the sanitary napkin, including the secondary absorbent member, or the flaps, or a separate component attached to the secondary absorbent member or the flaps.

The length SL, the width SW and the thickness ST of the secondary absorbent member 50 can be of any convenient dimension. The length SL is preferably from about 10 to 35 cm, and more preferably from about 20 to 35 cm. Preferably, the length SL of the secondary absorbent member 50 may be generally equal to the length PL of the primary absorbent member 30. The width SW is preferably from about 4 to 13 cm, more preferably from about 5 to about 11 cm, and most preferably from about 6 to about 9 cm. The secondary absorbent member 50 is preferably relatively thin and flexible. The thickness ST is preferably from about 0.1 to 2.0 cm, more preferably from about 0.1 to 1.0 cm, and most preferably from about 0.1 to 0.4 cm. Preferably, the thickness ST of the secondary absorbent member 50 may be less than the thickness PT of the primary absorbent member 30.

The secondary absorbent member (base member) 50 optionally may be manufactured without an absorbent core 56. Since most if not all of the bodily fluids are preferably absorbed by and are contained within the primary absorbent core 34 of the primary absorbent member 30, the base member 50 need only to protect the wearer's undergarments from soiling by relatively small amounts of fluids which may be expelled from the primary absorbent member 30 or which may inadvertently bypass the primary absorbent member 30. Accordingly, since the expected amounts of fluids which may come into contact with the base member are relatively small, an base core may not be necessary to contain the fluids within the base member 50 and prevent them from soiling the wearer'undergarments.

To form the compound sanitary napkin 20, the primary absorbent member 30 and the secondary absorbent member 50 are joined by union means generally indicated as 70 in FIGS. 1–3, 11 and 12. The union means 70 serves to join the primary absorbent member 30 and the secondary absorbent member 50 into the compound sanitary napkin 20 with sufficient tenacity that the primary absorbent member 30 and the secondary absorbent member 50 are not disconnected during use. Any suitable union means such as adhesive attachment, pressure attachment, heat attachment, or ultrasonic attachment can be used. The primary absorbent member 30 may be affixed to the secondary absorbent member 50 at least along not less than 10% of the longitudinal length of the primary absorbent member 30, preferably at the center in the longitudinal direction. Preferably, the primary absorbent member 30 may be affixed to the secondary absorbent member 50 at least along the length where the proximal edge 40 of the flaps 33 extends. More preferably, the primary absorbent member 30 may be affixed to said secondary absorbent member 50 by the union means 70 along the entire common length. Alternatively, the primary absorbent member 30 may be affixed to said secondary absorbent member 50 intermittently along the common length. In a preferred embodiment shown in FIGS. 1–3, 11 and 12, the primary absorbent member 30 is affixed to the secondary absorbent member 50 by the union means 70 including a first union means 72 and the second union means 74.

Figure 12:
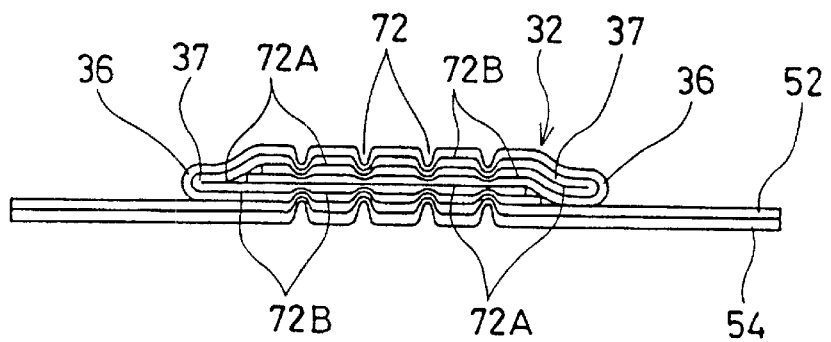
FIG. 12 is a cross-sectional view taken along XII—XII line shown in FIG. 1.

The first union means 72 includes applying pressure to the overlapped transverse ends 22 and 25 in plurality of discrete dots. By applying pressure at the overlapped transverse ends 22 and 25, the topsheet 32 of the primary absorbent member 30, the topsheet 52 and the backsheet 54 of the secondary absorbent member 50 are affixed to each other at the overlapped transverse ends 22 and 25. Alternatively, the first union means 72 can include applying heat in a plurality of discrete dots, lines or area. While applying heat works well to join mullet-layers, heat transfer between the layers to join the layers may become worse as the layers becomes thick. In the preferred embodiment shown in FIG. 2, since the longitudinal sides 45 of the topsheet 32 of the primary absorbent member 30 are overlapped to one another underneath the primary absorbent core 34, five layers comprising three layers of topsheet 32, one layer of the topsheet 52 and one layer of the backsheet 54 are joined. If the topsheet 32 comprises two layers having the formed film 36 and the nonwoven 37, eight layers must be joined to each other as shown in FIG. 12. As the layers becomes thick, it becomes preferable to apply pressure, or pressure and heat to join the layers. Alternatively, the first union means 72 may include applying adhesive between the layers, or applying combination of pressure, heat, and adhesive. In the preferred embodiment, adhesive 72A may be applied to the inside surface of the topsheet 32 at the transverse end 46 as shown in FIGS. 2 and 12. Alternatively, adhesive 72B may be applied between the formed film 36 and the nonwoven 37 at the transverse ends 44 and 48 as shown in FIG. 7. Alternatively, both the adhesive 72A and the adhesive 72B may be applied.

Figure 11:
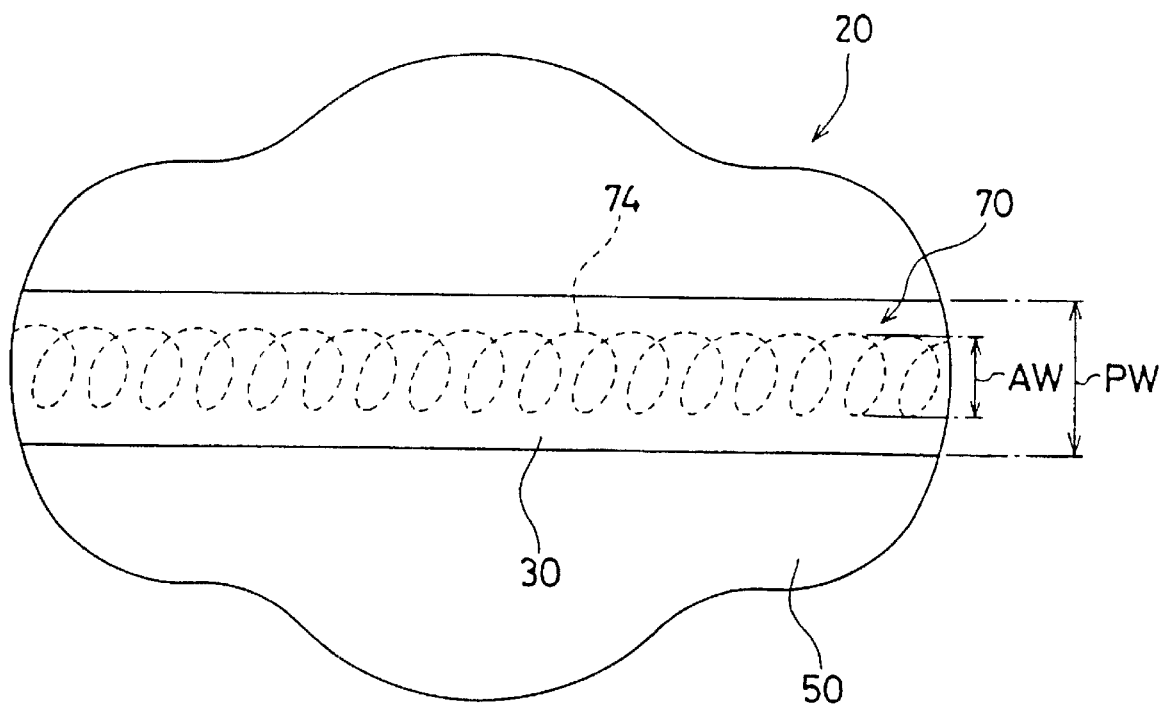
FIG. 11 is a top plan view a compound sanitary napkin comprising union means.

The second union means 74 includes applying adhesive such as spiral adhesive, line adhesive, or spot adhesive between the primary absorbent member 30 and the secondary absorbent member 50. As shown in FIG. 11, in a preferred embodiment, spiral adhesive 74 as the second union means is applied continuously between the primary absorbent member 30 and the secondary absorbent member 50 to attach the primary absorbent member 30 with the topsheet 52 of the secondary absorbent member 50. When the primary absorbent member 30 and the secondary absorbent member 50 are desired to affix to one another along the entire common length, it is preferable to use spiral adhesive since applying spiral adhesive prevents the absorbent member 30 and 50 from affixing intermittently. The primary absorbent member 30 and the secondary absorbent member 50 are preferably affixed at the narrower width AW than the transverse width PW of the primary absorbent member 30. Preferably, the width AW may be less than 70% of the width PW. This allows the primary absorbent member 30 to conform with the female body shape and movement of the female body.

The compound sanitary napkin 20 of the present invention is utilized by removing the release liners 59 and 63 and placing the compound sanitary napkin 20 in a undergarment 82 as shown in FIG. 13 The secondary absorbent member 50 is placed in the crotch portion of the undergarment with one end of the secondary absorbent member 50 extending towards the front section of the undergarment and the other end towards the back section of the undergarment. The backsheet 54 is placed in contact with the inner surface of the center of the crotch portion of the undergarment 82. The central pad adhesive fastener 58 maintains the compound sanitary napkin 20 in position. The distal portions of the flaps 33 are folded around the side edges 80 of the undergarment 82. The flap adhesives 62 secure the flaps 33 to the underside of the undergarment or to the opposing flap. The primary absorbent member 30 joined to the secondary absorbent member held on the undergarment 82 by the flaps stays adjacent to the wearer's body where the exudates which are discharged from the body are expected. During the compound sanitary napkin 20 is worn, a portion of the primary absorbent member 30 may shift away from the flap 33 as shown by the arrow A in FIG. 13. Such shifting may give a stress to the flap 33 so that the flap 33 detach from the undergarment. Since the zones of extensibility 66 is extensible being capable of the stress given to the flap 33, the flaps 33 are substantially free from shifting when the portion of the primary absorbent member 30 shifts with the wearer's body.

Figure 14:
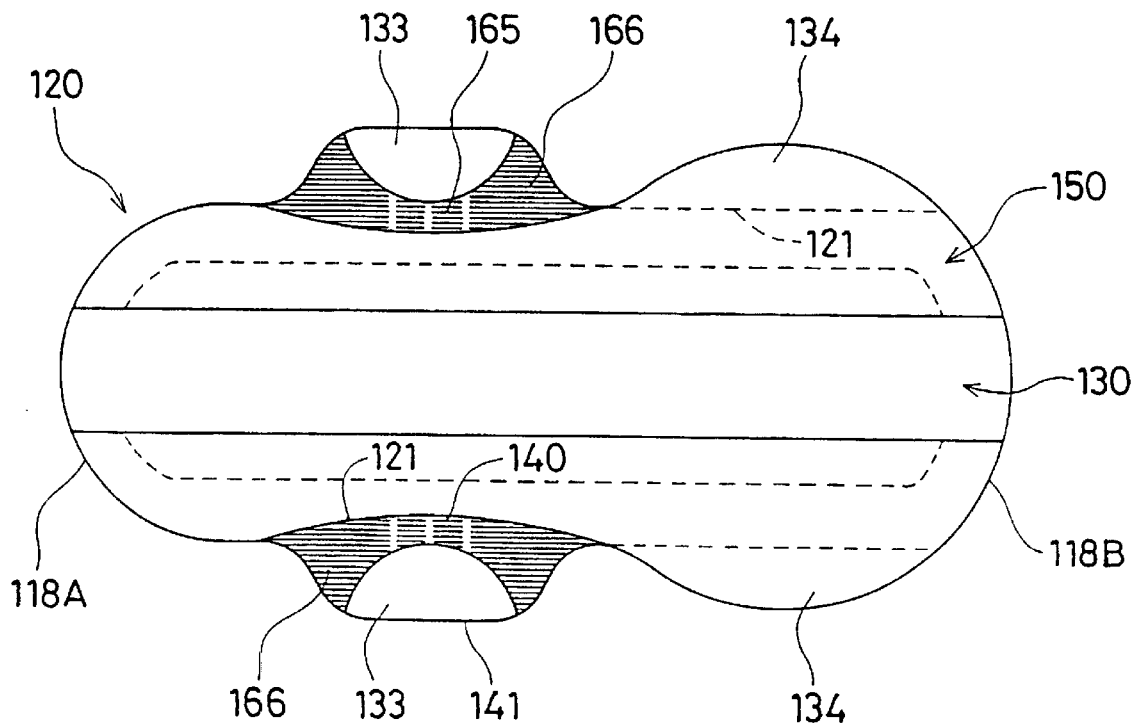
FIG. 14 is a top plan view of another embodiment of a compound sanitary napkin of the present invention.

FIG. 14 shows another preferred embodiment of the present invention. In FIG. 14, the compound sanitary napkin 120 may comprise a primary absorbent member 130, the secondary absorbent member 150, the flaps (or first flaps) 133 and the additional flaps (or second flaps) 134. The compound sanitary napkin 120 may have longer length than the compound sanitary napkin 20 shown in FIG. 1 since the compound sanitary napkin 120 has the second flaps 134. The first flaps 133 may be biased toward one transverse end 118A of the compound sanitary napkin 20 and have the proximal edge 140 and the distal edge 141. Preferably, the entire length of the proximal edge 140 may be not less than 20% of the length of the primary absorbent member 130. At the opposite transverse end 118B, the second flaps 134 may extend laterally outward beyond the longitudinal sides 121 of the secondary absorbent member 150. The second flaps 134 stay widespread in the wearer's undergarment when the compound sanitary napkin 120 is worn. The first flaps 134 may comprise the same component as the first flaps 133 and may be joined to the secondary absorbent member 150 by the same method. Preferably, the second flaps 134 may comprise the extensions of the topsheet and the backsheet of the secondary absorbent member 150. The compound sanitary napkin 120 are provided with the hinge 165 between the secondary absorbent member 150 and at least the portion of the flaps 133. The secondary absorbent member 150 of the compound sanitary napkin 120 preferably has four zones of extensibility 166 on the first flaps 133.

It may be desirable to provide a compound sanitary napkin having a primary absorbent member with varying degrees of width or caliper throughout its length. For example, the primary absorbent member may be relatively thicker in the central region as opposed to the end regions. Alternatively, the primary absorbent member may be relatively thinner in the central region as opposed to the end regions.

While particular embodiments of the present invention have been illustrated and described, it would be obvious to those skilled in the art that various other changes and modifications can be made without departing from the spirit and scope of the invention. It is therefore intended to cover the appended claims all such changes and modifications that are within the scope of this invention.

What is claimed is:

1. A compound sanitary napkin having a longitudinal center line along a longitudinal direction and a transverse center line along a transverse direction the sanitary napkin comprising:
   (a) a primary absorbent member having a longitudinal length, a transverse width, a thickness, a pair of longitudinal sides and a pair of transverse ends, and comprising a primary absorbent element and a fluid pervious cover superimposed on the primary absorbent element;
   (b) a base member having a longitudinal length, a transverse width, at thickness, a pair of longitudinal sides and a pair of transverse ends, and comprising a fluid pervious body-facing sheet and fluid impervious garment-facing sheet joined to the fluid pervious body-facing sheet, and the primary absorbent member joined to the base member at least at a part of the longitudinal direction of the primary absorbent member;
   (c) flaps extending laterally outwardly from the longitudinal sides of the base member, each of the flaps having a proximal edge joined with the longitudinal sides of base member and a distal edge spaced laterally outwardly from the proximal edge, the flaps covering a portion of the leg openings of the wearer's undergarment, the flaps are biased toward one transverse end of the base member, and additional flaps are provided along the longitudinal sides of the base member adjacent to the other transverse end of the base member;
   (d) at least one zone of extensibility comprising a least a portion of the flaps, wherein at least a portion of the zone of extensibility is spaced longitudinally away from the flap transverse centerline, wherein
   (e) the entire length of the proximal edge of the flaps is not less than 20% of the length of the primary absorbent member; and
   (f) at least the zone of extensibility is extensible to be capable of a stress given to the flap when the compound sanitary napkin is worn so that the flaps are relatively free from shifting when at least a portion of the primary absorbent members shifts away from the flap.

2. The compound sanitary napkin of claim 1 wherein the compound sanitary napkin further includes a hinge comprising a portion of the compound sanitary napkin between the base member and the flaps.

3. The compound sanitary napkin of claim 1 wherein the primary absorbent member is joined to the body-facing sheet of the base member along the length of not less than 10% of the longitudinal length of the primary absorbent member.

4. The compound sanitary napkin of claim 3 wherein the primary absorbent member is joined to the body-facing sheet of the base member at least along the length of the proximal edge of the flaps.

5. The compound sanitary napkin of claim 4 wherein the flap comprises an extending portions of the fluid pervious body-facing sheet and the fluid impervious garment-facing sheet, and the hinge and the zone of extensibility are provided the extending portions of the fluid pervious body-facing sheet and the fluid impervious garment-facing sheet.

6. The compound sanitary napkin of claim 5 wherein the zone of extensibility has a direction of extensibility, the zone of the extensibility is provided so that the direction is disposed at an angle to the longitudinal direction of the primary absorbent member.

7. The compound sanitary napkin of claim 6 wherein the zone of extensibility comprises a plurality of corrugations, the corrugations comprise ridges that are generally oriented in the longitudinal direction of the primary absorbent member.

8. The compound sanitary napkin of claim 6 wherein the zone of extensibility comprises a plurality of corrugations, the corrugations comprise ridges that are oriented at an angle to the longitudinal direction of the primary absorbent member.

9. The compound sanitary napkin of claim 1 wherein the flaps generally position in the longitudinal center of the primary absorbent member.

* * * * *